United States Patent [19]

Kanikanti et al.

[11] Patent Number: 5,707,655
[45] Date of Patent: Jan. 13, 1998

[54] PROCESS FOR THE PREPARATION OF MEDICAMENT FORMULATIONS WITH CONTROLLED RELEASE

[75] Inventors: Venkata-Rangarao Kanikanti; Stefan Kettelhoit, both of Leverkusen; Peter Kurka, Langenfeld; Gunther Penners, Leverkusen; Peter Serno, Bergisch Gladbach, all of Germany

[73] Assignee: Bayer Aktiengesellschaft, Leverkusen, Germany

[21] Appl. No.: 701,410

[22] Filed: Aug. 22, 1996

[30] Foreign Application Priority Data

Aug. 29, 1995 [DE] Germany .................. 195 31 684.3

[51] Int. Cl.⁶ .................................................. A61K 9/22
[52] U.S. Cl. .................. 424/468; 424/500; 424/501
[58] Field of Search ........................ 424/489, 468, 424/500, 501

[56] References Cited

U.S. PATENT DOCUMENTS

| | | | |
|---|---|---|---|
| 4,412,986 | 11/1983 | Kawata et al. | 514/772 |
| 4,992,278 | 2/1991 | Khanna | 424/473 |
| 5,231,070 | 7/1993 | Narayanan et al. | 504/113 |
| 5,286,493 | 2/1994 | Oshlack et al. | 424/468 |

FOREIGN PATENT DOCUMENTS 0232155  8/1987  European Pat. Off.

OTHER PUBLICATIONS

Derwent Abstract, Abstract of JP 06-172,160, Derwent Week 9429 (1994).

*Primary Examiner*—Peter F. Kulkosky
*Attorney, Agent, or Firm*—Sprung Kramer Schaefer & Briscoe

[57] ABSTRACT

The invention relates to a special process for the preparation of stable, solid medicament formulations of high bioavailability and with controlled release comprising sparingly soluble active compounds and polymeric auxiliaries, and to the formulations thus prepared.

9 Claims, No Drawings

PROCESS FOR THE PREPARATION OF MEDICAMENT FORMULATIONS WITH CONTROLLED RELEASE

The invention relates to a special process for the preparation of stable, solid medicament formulations of high bioavailability and controlled release comprising sparingly soluble active compounds and polymeric auxiliaries, and to the formulations thus prepared.

Solid solutions or coprecipitates of active compounds such as, for example, dihydropyridines and polyvinyllactams are known. They can be prepared, for example, by dissolving the active compound and auxiliary together in organic solvents and further processing the solution to tablets or by shaping an active compound/auxiliary melt, for example by injection moulding or extrusion and subsequent calendering.

Preparation via organic solutions involves the following problems: suitable organic solvents, such as chlorinated hydrocarbons, ketones or alcohols, pollute the environment and must therefore be recovered, with great technical expenditure, during or after the separation of solid solutions. If solvents which form explosive or ignitable mixtures with air are used, the entire process must proceed under explosion protection. Large amounts of auxiliaries are required, since the organic solution of the active compound and polymer must be adsorbed onto a carrier, for example a crosslinked polymer, for further shaping of the medicament (cf. EP 0 232 155). Complete removal of the solvent used from the product is usually expensive or impossible, so that an undesirable content of residual solvents remains in the product. Coprecipitates prepared in this way often tend towards recrystallization of the active compound and are therefore not stable to storage, or do not show a constant bioavailability over a storage period of several months.

The preparation of solid solutions by intimate mixing of the active compound with a polymer melt and subsequent processing of the melt, with shaping, to give solid pieces (for example EP 0 596 203) has also proved to have disadvantages.

If the active compound is mixed with the melt in single- and twin-screw extruders and the extrudate is subsequently shaped on calender rolls, the shape of the pieces which it is possible to achieve is limited by process technology. In particular, the cylindrical tablet shape with a ridge on the side, which is familiar to the patient, cannot be produced or can be produced only with great limitations. This results in a reduced acceptance of the medication and involves the risk that the resulting pieces of circular or cushion-shaped cross-section will be mistaken for sweets.

If mixing of the active compound with the melt and shaping are carried out by the injection moulding process, other disadvantages, such as, for example, a low cycle number of the process, must be accepted.

The process described in EP 0 596 203 for intimate mixing of an active compound with a polymer melt and subsequent shaping furthermore has considerable limitations with respect to the polymers which can be used. Thus—as described there—the polymers employed must lie within certain viscosity levels. Furthermore, at least one of the two polymers employed must have a sufficiently low viscosity in molten form so that shaping is still possible at all. As a consequence of these limitations, the polymers which would be optimum in the context of effective release control cannot be employed, and medicament forms result which are comparatively large and are thus unpleasant for the patient.

The present invention was based on the object of overcoming the limitations of process technology mentioned above. The problems are solved by the new process, which relates to the preparation of medicament formulations by granulation or tableting of powders or granules by customary methods and subsequent thermal dissolution or amorphization of the active compound. The shaping of the first process step by pressing (tableting) or granulation allows a considerably more advantageous choice of polymers here. The ready-shaped medicament formulation is then heated in a subsequent process step which is easy to carry out.

The invention thus relates to the preparation of solid medicament formulations comprising one part by weight of one or more sparingly soluble active compounds (I), 0.5 to 50 parts by weight, preferably up to 20 parts by weight, of a cellulose ether (II) and 0.5 to 50 parts by weight, preferably up to 20 parts by weight, of polyvinyllactams or polyvinyllactam copolymers (III) and, if appropriate, other customary auxiliaries, characterized in that the constituents (I), (II) and (III) are mixed in the absence of solvents and the mixture is shaped to give the desired medicament formulations, and these are then activated by means of heat at temperatures between 50° and 200° C., preferably at 80° to 170° C., for at least 30 minutes.

Preferred solid medicament formulations which may be mentioned are tablets, pellets and granules, in particular tablets.

The duration of the heat treatment is at least 30 minutes and can be up to 3 days, preferably up to 48 hours, depending on the temperature chosen.

The cellulose ethers (II) employed according to the invention are preferably compounds based on linear alkoxylated cellulose compounds, which are employed in amounts of between 5 and 60% by weight, preferably between 20 and 45% by weight, based on the weight of the ready-to-use formulation. Particularly preferred cellulose ethers are compounds having methoxy and hydroxypropyl substituents, which have a viscosity of 15 to 100,000 mPa○s, preferably 50 to 30,000 mPa○s, in 2% strength aqueous solutions, for example the products known by the trade names Metolose 60 SH, Metolose 65 SH and Metolose 90 SH.

The polyvinyllactams (III) employed according to the invention are preferably high molecular weight compounds based on polyvinylpyrrolidone or vinylpyrrolidone/vinyl acetate copolymer which have an average molecular weight (weight-average $\overline{MW}$) of 20,000 to 2,000,000, preferably 25,000 to 1,500,000 $\overline{MW}$ and are employed in amounts of between 5 and 60% by weight, preferably between 20 and 40% by weight, based on the final weight of the medicament formulation. Linear polyvinylpyrrolidones having a high molecular weight, for example those known by the trade names Kollidon K25, Kollidon 90 and Kollidon VA 64, are particularly preferred.

All heat-stable active compounds can be incorporated into the formulations prepared according to the invention. Sparingly soluble active compounds, in particular those from the group of dihydropyridines, may be mentioned as preferred. These active compounds are preferably employed proportionately in amounts of 5 to 50% by weight, preferably 20 to 35% by weight, of the finished formulation.

In contrast to the processes known to date for solvent-free preparation of solid solutions by means of heat, in which there was always the need for intensive mechanical mixing of the active compound with the polymer melt, for example by a screw extruder, the route of preparing a solid solution from a preshaped system of a compressed tablet of powder or granules by heat treatment without further mechanical action is taken for the first time in the present invention. This process has the advantage that relatively simple preparation apparatus which have been customary to date, such as tableting machines or drying apparatus, can be used. The process furthermore allows choice of the most effective polymers possible, regardless of the need for shaping of the melt. As a consequence, tablets which are considerably smaller and lighter in weight can be produced, with the advantages of being easier to swallow for the patient, economical use of pharmacologically inactive auxiliaries and also small tablet packs, which require less storage area and transportation space. The formulations prepared according to the invention furthermore also have pharmacological advantages because of the absence of undesirable solvent residues and the small amounts of auxiliaries.

It is known that coprecipitates prepared with solvents show recrystallization of the sparingly soluble active compounds even after a short time during prolonged storage, in particular under adverse conditions, such as, for example, high atmospheric humidity or elevated temperature (tropics), which leads to a reduction in bioavailability. The solvent-free formulations activated by heat according to the invention show a significantly higher storage stability and a bioavailability which remains constantly good for several months.

The process according to the invention can particularly preferably be used for the preparation of formulations with controlled release of active compounds, in particular for sustained release formulations, which are intended to release the active compound linearly over several hours.

EXAMPLES 1 to 4

The following commercially obtainable polymers were used for preparation of the formulations according to the invention:

Polymer (III):
   Polyvinylpyrrolidone K 25 (Kollidon® 25)
   Polyvinylpyrrolidone K 90 (Luviskol® K90)
Polymer (II):
   Hydroxypropylmethylcelluose Type 2910 USP of viscosity level 50 mPaos (Metolose® 60 SH 50)
Active compound (I):
   Nimodipine was used as the active compound.

The substances shown under Examples 1 to 4 in Table 1 were mixed and tablets of the stated format and weight were produced by means of a customary tableting press. The activation by means of heat was carded out at 140° C. for 4 hours. The release of the active compound was determined in a customary release apparatus (paddle method). For this, the tablets were incubated in a buffer of pH=6.8 at 37° C. and 150 rpm. The tablets release the active compound according to Table 1 in the course of 6 hours.

TABLE 1

| | Example | | | |
|---|---|---|---|---|
| | 1 | 2 | 3 | 4/100 rpm |
| Drug (I) | nimodipine 90 mg (33.33%) | nimodipine 90 mg (33.33%) | nimodipine 90 mg (33.0%) | nimodipine 45 mg (33.3%) |
| Polymer (III) | PVP K 90 66.22 mg (24.5 %) | PVP K 90 107.57 mg (39.8%) | PVP K 90 86.46 mg (31.7%) | PVP K 90 53.81 mg (39.8%) |
| Polymer (II) | Metolose® 60 SH 50 113.24 mg (41.9%) | Metolose® 60 SH 50 71.89 mg (26.6%) | Metolose® 60 SH 50 95.46 mg (35%) | Metolose® 60 SH 50 35.96 mg (26.6%) |

TABLE 1-continued

| | Example | | | |
|---|---|---|---|---|
| | 1 | 2 | 3 | 4/100 rpm |
| Mg stearate | 0.81 mg (0.3%) | 0.81 mg (0.3%) | 0.82 mg (0.3%) | 0.41 mg (0.3%) |
| Tablet weight | 270.27 mg | 270.27 mg | 272.73 mg | 135.18 mg |
| Tablet format | 10 r 15 | 10 r 15 | 10 r 15 | 8 r 12 |
| Release | | | | |
| 60 min. | 16% | 30% | 22% | 31% |
| 120 min. | 34% | 54% | 44% | 60% |
| 180 min. | 52% | 73% | 63% | 83% |
| 240 min. | 66% | 86% | 77% | 95% |
| 300 min. | 78% | 90% | 87% | 99% |
| 360 min. | 87% | 92% | 93% | 100% |

All the examples of recipes listed show virtually complete uniform (linear) release of the active compound over 6 hours. The polyvinyllactams used bring about effective solubilization and, together with the hydroxypropylcellulose employed, retard the release of the active compound over several hours. By using high molecular weight polyvinyllactams, high drug doses can also be solubilized effectively at a low tablet weight. It is therefore ensured that the tablets are easy to swallow.

Comparison Example 1 to EXAMPLE No. 4
(Without Amorphization by Means of Heat)

The recipe from Example 4 was tableted under identical conditions, but without subsequently carrying out the amorphization by means of heat. The active compound was released under conditions identical to those above.

TABLE 2

| Comparison Example 1 | |
|---|---|
| Drug (I) | Nimodipine 45 mg (33.3%) |
| Polymer (III) | PVP K 90 53.81 mg (39.8%) |
| Polymer (II) | HPMC 60 SH 50 35.96 mg (26.6%) |
| Mg stearate | 0.41 mg (0.3%) |
| Tablet weight | 135.18 mg |
| Tablet format | 8 r 12 |
| Release | |
| 60 min. | 5% |
| 120 min. | 12% |
| 180 min. | 18% |
| 240 min. | 21% |
| 300 min. | 25% |
| 360 min. | 25% |

The tablet releases the active compound contained therein only extremely incompletely.

Comparison Example 2 to EXAMPLE Nos. 1 to 4
(Solvent Process)

A tablet containing the active compound was produced by a solvent process. Specifically, an acetone solution of nimodipine in PVP K 25 was adsorbed onto Crospovidone M and tablets were then produced with Metolose® 60 SH 50 and lactose. No amorphization by means of heat was carried out. The active compound was released under conditions identical to those described above.

TABLE 3

| Comparison Example 2 | |
| --- | --- |
| Drug (I) | nimodipine 45 mg (11.75%) |
| Polymer (III) | PVP K 25 112.5 mg (29.37%) |
| Polymer (II) | Crospovidone M 45 mg (11.75%) |
| | Metolose ® 60 SH 50 160 mg (41.78%) |
| | lactose 19.5 mg (5.09%) |
| Mg stearate | 1 mg (0.26%) |
| Tablet weight | 383 mg |
| Tablet format | 11 r 18 |
| Release | |
| 60 min. | 17% |
| 120 min. | 43% |
| 180 min. | 68% |
| 240 min. | 90% |
| 300 min. | 102% |
| 360 min. | 101% |

The tablet completely releases the active compound contained therein. The preparation process must be carried out in an expensive manner under explosion protection and in a vacuum fluidized bed during the granulation with acetone. The tablet is virtually three times as heavy as and significantly larger than the tablets of Examples 1 to 4 produced by the process according to the invention.

Comparison Example 3 to EXAMPLE Nos. 1 to 4 (Extrusion Process)

A tablet containing the active compound was produced by an extrusion process. Specifically, a mixture of nimodipine, PVP K 25 and Crospovidone M was extruded at 156° C. through a twin-screw machine with the screws rotating in opposite directions, and tablets were then produced with Metolose® 60 SH 50 and lactose. No heat treatment of the tablets was carried out. The active compound was released under conditions identical to those described above.

TABLE 4

| Comparison Example 3 | |
| --- | --- |
| Drug (I) | Nimodipine 45 mg (11.75%) |
| Polymer (III) | PVP K 25 112.5 mg (29.37%) |
| | Crospovidone M 45 mg (11.75%) |
| Polymer (II) | Metolose ® (41.78%) |
| | lactose 19.5 mg (5.09%) |
| Mg stearate | 1 mg (0.26%) |
| Tablet weight | 383 mg |
| Tablet format | 11 r 18 |
| Release | |
| 60 min. | 26% |
| 120 min. | 61% |
| 180 min. | 88% |
| 240 min. | 90% |
| 300 min. | 91% |
| 360 min. | 90% |

The tablet releases the active compound contained therein virtually completely. To achieve the release profile, about 3.8 times more polymer mass is required compared with Example 4. The preparation process is expensive in terms of apparatus.

EXAMPLES 5 and 6

The following commercially obtainable polymers were used to prepare the formulations according to the invention:

Polymer (III)
Polyvinylpyrrolidone K 90
(Luviskol® K90)
Copolymer of 60% of N-vinylpyrrolidone and 40% of vinyl acetate
(Kollidon® VA 64)
Polymer (II)
Hydroxypropylmethylcellulose
Type 2910 USP of viscosity level 50 mPa○s (Metolose® 60 SH 50)
Hydroxypropylmethylcellulose Type 2906 USP of viscosity level 4000 mPa○s (Metolose® 65 SH 4000)

The substances shown under Examples 5 and 6 in Table 5 were mixed and tablets of the stated format and weight were produced by means of a customary tablet press. The activation by means of heat was carried out at 170° C. for 2 hours. The release of the active compound was determined in a customary release apparatus by the paddle method. For this, the tablets were incubated in a buffer of pH 6.8 at 37° C. and 100 rpm. The tablets release the active compound according to Table 5 in the course of 8 hours.

TABLE 5

| | Comparison Example | |
| --- | --- | --- |
| | 5 | 6 |
| Drug (I) | Nifedipine 62.5 mg (24.8%) | Nifedipine 60.0 mg (20%) |
| Polymer (III) | PVP K 90 94.125 mg (37.35%) | Kollidon ® VA 64 119.25 mg (39.75%) |
| Polymer (II) | Metolose ® 60 SH 50 94.125 mg (37.35%) | Metolose ® 65 SH 4000 119.25 mg (39.75%) |
| Mg stearate | 1.25 mg (0.5%) | 1.5 mg (0.5%) |
| Tablet weight | 252 mg | 300 mg |
| Tablet format | 10 mm | 10 mm |
| Release | | |
| 60 min. | 8% | 6% |
| 120 min. | 12% | 11% |
| 180 min. | 16% | 17% |
| 240 min. | 19% | 25% |
| 300 min. | 21% | 35% |
| 360 min. | 24% | 46% |
| 420 min. | 25% | 57% |
| 480 min. | 27% | 67% |

We claim:

1. A process for preparing a controlled release, solid medicament formulations which possess high stability, said process comprises:

A. mixing in the absence of solvents at least three components which comprise
   at least one part by weight of a sparingly soluble and heat-stable active compound (I);
   0.5 to 50 parts by weight of a cellulose ether (II); and
   0.5 to 50 parts by weight of a polyoctam or polyvinyl-lactam copolymer (III)

B. shaping the solid mixture obtained above to give the desired medicament formulation; and C. heating the shaped formulation obtained above at a temperature between 50° and 200° C. for at least 30 minutes to achieve thermal dissolution or amorphization of the active compound.

2. The process according to claim 1, characterized in that cellulose ethers having methoxy and hydroxypropyl substituents which have a viscosity of 15 to 100,000 mPa○s in 2% strength aqueous solution are employed as constituent (II).

3. The process according to claim 1, characterized in that polyvinylpyrrolidone or vinylpyrrolidone/vinyl acetate copolymer which has an average molecular weight of 20,000 to 2,000,000 $\overline{MW}$ is employed as constituent (III).

4. Solid medicament formulations prepared according to the process of claim 1.

5. The process according to claim 1, wherein the heating step is carried out at a temperature of 80° to 170° C. for a time period of 30 minutes to 48 hours.

6. The process according to claim 1, wherein the sparingly soluble active compound is a dihydropyridine.

7. The process according to claim 1, wherein the solid medicament formulation is in the shape of a tablet, pellet or granules.

8. The process according to claim 1, wherein the heating step is carried out at a temperature between 50° and 200° C. for a time period of 30 minutes to 72 hours.

9. The process according to claim 1 wherein
  A. mixing in the absence of solvents three components which comprise
     5 to 50 parts by weight of a dihydropyridine compound,
     20 to 45 parts by weight of a cellulose ether having methoxy and hydroxypropyl substituents and having a viscosity of 15 to 100,000 mPa·s in a 2% strength aqueous solution; and
     20 to 40 parts by weight of a polyvinylpyrrolidone or vinylpyrrolidone/vinyl acetate copolymer, which has an average molecular weight of 20,000 to 2,000,000 $\overline{MW}$;
  B. shaping the mixture obtained above into a tablet; and
  C. heating the tablet obtained above at a temperature of 80° C. to 170° C. for a time period between 30 minutes and 48 hours to achieve thermal dissolution or amorphization of the active compound.

\* \* \* \* \*